United States Patent [19]

Speiser

[11] Patent Number: 5,691,164
[45] Date of Patent: Nov. 25, 1997

[54] TISSUE FIXATIVE COMPRISING AN AQUEOUS SOLUTION OF ETHANOL, ETHANDIOL, METHANAL, NACL AND $ZNCL_2$

[75] Inventor: Eric N. Speiser, St. Petersburg, Fla.

[73] Assignee: Aaron Medical Industries, Inc., St. Petersburg, Fla.

[21] Appl. No.: 563,192

[22] Filed: Nov. 27, 1995

[51] Int. Cl.$^6$ .................... C12Q 1/08; A01N 1/00; A01N 3/00
[52] U.S. Cl. .................... 435/40.52; 435/40.5; 428/22
[58] Field of Search .................... 428/22; 435/2, 435/40.52, 40.5

[56] References Cited

U.S. PATENT DOCUMENTS

| | | | |
|---|---|---|---|
| 4,248,734 | 2/1981 | Romero-Sierra et al. | 252/400 R |
| 4,278,715 | 7/1981 | Romero-Sierra et al. | 428/22 |
| 4,328,256 | 5/1982 | Romero-Sierra et al. | 427/4 |
| 4,828,890 | 5/1989 | Tiedeman et al. | 428/22 |

FOREIGN PATENT DOCUMENTS 7126102 5/1995 Japan .

*Primary Examiner*—Sandra E. Saucier
*Attorney, Agent, or Firm*—Arthur W. Fisher, III

[57] ABSTRACT

A tissue fixative comprising a solvent including one or more alkanols, one or more diols and/or triols and a catalyst, and a solute including an osmotically active substance and a mordant. A preferred composition comprises 14 ml ethanol, 14 ml ethandiol, 2.43 ml of a 37% solution of methanal, 0.375 g NaCl, 0.0375 g $ZaCl_2$ and 69.57 mls water.

1 Claim, No Drawings

TISSUE FIXATIVE COMPRISING AN AQUEOUS SOLUTION OF ETHANOL, ETHANDIOL, METHANAL, NACL AND ZNCL$_2$

BACKGROUND OF THE INVENTION

1. Field of the Invention:

A water based non-toxic, non-carcinogenic tissue fixative.

2. Description of the Prior Art:

Histologists have long endeavored to develop effective immunohistochemical fixatives and morphologic fixatives. Moreover it is desirable to preserve morphologic detail preserve tissue antigens to permit immunohistochemical detection and localization of antigens in tissue.

Such fixatives render protein insoluble. For example, formaldehyde may be used as a crosslinking agent forming covalent bonds between the aldehyde groups and specific amino acids to stabilize protein structure and transform the cell cytoplasm into a gel which prohibits movement of autolytic enzymes. Alternately, alcohol may be used as a fixative to precipitate protein through denaturation.

Preferably, a fixative should retard autolysis and putrefaction and preserve morphologic detail and antigenicity. Unfortunately, an effective morphologic fixative is not necessarily an effective immunohistochemical fixative.

U.S. Pat. No. 5,196,182 describes tissue fixatives such as diazolidinyl urea which are free of aldehydes and toxic chemicals used in aqueous or alcoholic solutions for good tissue preservation. Further, tissue antigens are retained rendering the fixative useful in immunostaining procedures.

U.S. Pat. No. 4,248,734 shows a solution and process for preserving Douglas Fir needles and preventing shedding to produce a natural looking product suitable for display purposes. The branches and needles are immersed in a solution comprising by volume: 300–500 ml water; 200–300 ml ethyl alcohol; 0–75 ml ethylene glycol; 50–75 ml propionic acid; 0–20 ml glycerin; 100–150 ml formalin; 50–175 ml propylene glycol; 40–75 gms citric acid; 1–7 gms magnesium sulphate; 15–25 gms cupric Sulphate; 5–10 gms sodium sulphite; and 0–10 gms seaweed extract, for a period of up to about two weeks and subsequently air dried.

U.S. Pat. No. 4,278,715 teaches a process for preserving green colored plant tissues while retaining the natural green color thereof. The tissues are immersed in a solution comprising: water, at least one monohydric alcohol, at least one preservative component selected from the group comprising lower carboxylic acids, di and tri hydric alcohols, and sufficient buffering and mordant reagents to control the pH and osmolality of the solution, so as to permanently retain the green color in the tissues. In a preferred embodiment, the treated tissue is subjected to a secondary treatment in a holding solution comprising glycerin and water.

U.S. Pat. No. 4,328,256 describes a process for preserving green colored plant tissues and in particular coniferous needles, holly and low fiber leaves such as mosses, lichens and ferns in which selected leaves are immersed in a solution comprising by volume: 35–45 percent water, 20–30 percent 2-propanol, 5–12 percent propionic acid, 5–10 percent sulphurous acid, 5–10 percent formalin, 2.5–5 percent formic acid, 1–5 percent ethylene glycol, and optionally minor amounts of compounds selected from the group consisting of cupric sulphate, cupric chloride, 20-20-20 fertilizer, citric acid, DBE, magnesium sulphate, acetic acid, cupric acetate, cupric nitrate, sodium phosphate, sodium sulfite, butylated hydroxytoluene and glycerol, for a sufficient time to exchange the naturally occurring water in the tissues with the chemical water of the solution to permanently retain and biologically fix the green color of the leaves.

U.S. Pat. No. 4,946,669 shows a mercury and formaldehyde free histological fixative comprising one or more alkanols, one or more diols and triols such as ethylene glycol, and one or more acids such as acetic and formic acid in an aqueous solution. A salt of a metal ion having an oxidation state of at least two may be added as an optional mordant. Osmotically active substances such as sodium chloride may be used as an option as desired to control osmotically induced cell volume changes.

SUMMARY OF THE INVENTION

The present invention relates to a non-carcinogenic, environmentally safe water based, non-toxic tissue fixative formulated to replace formalin in most tissue/cell fixation applications where specimen sizes are about 6 mm in thickness or less. The tissue fixative of the present invention is equally useful in immunohistochemical procedures. Experimentation has established that the penetration rate is about 1 mm per hour to a maximum of about 13 mm in 24 hours. As such the present invention is not recommended for fixing large sections or organs. Whole organs or large sections/tissue blocks must still be sectioned or sliced in increments of about ¼ inch to about ½ inch.

In addition to being compatible with and safe for use in all current model tissue processors, the tissue fixative of the present invention exhibits the following advantages: equivalent penetration and shorter staining times compared to formalin; reduced tissue-to-fixative volume 1.5 versus 1.10 for formalin, preservation of antigenic properties of proteins; morphology and nuclear detail comparable or better than that of formalin; disposable in the same manner as alcohol; and excellent for immunohistochemical procedures.

The tissue fixative comprises a solvent of one or more alkanols, one or more diols and/or triols and a catalyst, and a solute including an osmotically active substance and a mordant.

The following is an example of the formulation of the tissue fixative of the present invention: ethyl alcohol; ethanediol, methanal; sodium chloride; zinc chloride, and deionized water.

So formulated, the tissue fixative of the present invention can be used effectively as a morphologic fixative or immunohistochemical fixative for specimens of about 13 mm in thickness or less.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

The present invention relates to an water based, non-toxic tissue fixative formulated to replace formalin in many tissue/cell fixation applications. Experimentation has established that the penetration rate is about 1 mm per hour to a maximum of about 13 mm in 24 hours. Therefore, whole organs or large sections/tissue blocks must still be sliced or sectioned.

The tissue fixative comprises a solvent of one or more alkanols to penetrate the tissue, dehydrate the cells and inhibit bacterial and vital activity, one or more diols and/or triols to expedite the dehydration of the tissue during fixation and enhance microscopic detail of the cell nuclei and a catalyst to increase the rate of penetration of the alkanols, diols and/or triols and deliver the solutions constituents into the tissue to be preserved and improve nuclear morphological detail and a solute including an osmotically active substance to regulate cell volume changes and a mordant to enhance stain and aid in osmotic regulation of cell volume and deionized water to maintain the salts solubility and support the osmotically active substances during tissue fixation.

The alkanol is selected from a group consisting of methanol and ethanol, the diol or triol is selected from a group consisting of ethylene glycol, glycerol, propylene glycol and trimethylene glycol and the catalyst is selected from a group including methanal.

The osmotically active agent is selected from a group consisting of sodium chloride, zinc chloride, and sugars such as poly saccharides, sucrose and glucose.

The mordant is selected from a group consisting of a salt with metal ion having an oxidation state of at least two including zinc chloride, strontium, calcium, barium and chromium.

The zinc chloride may also be used in the dual function of the mordant and osmotically active agent.

The preferred portional relationship of the ingredients of the tissue fixative is about 14.0 ml of ethyl alcohol, about 14.0 ml of ethanediol, about 2.43 ml of methanal 37%, about 375 g of sodium chloride, about 0.0375 g of zinc chloride and about 69.57 ml of deionized water.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A tissue fixative comprising about 14 ml ethanol, about 14 ml ethandiol, about 2.43 ml of a 37% solution of methanal, about 0.375 g NaCl, about 0.0375 g $ZnCl_2$ and about 69.57 mls water and proportional relationships thereof.

* * * * *